(12) United States Patent
Whitson (10) Patent No.: US 6,561,989 B2
(45) Date of Patent: May 13, 2003

(54) THIN LANCE AND TEST SENSOR HAVING SAME

(75) Inventor: Robert C. Whitson, Goshen, IN (US)

(73) Assignee: Bayer Healthcare, LLC, Elkart, IN (US)

( * ) Notice: Subject to any disclaimer, the term of this patent is extended or adjusted under 35 U.S.C. 154(b) by 0 days.

(21) Appl. No.: 09/877,420

(22) Filed: Jun. 11, 2001

(65) Prior Publication Data

US 2002/0004196 A1 Jan. 10, 2002

Related U.S. Application Data

(60) Provisional application No. 60/216,972, filed on Jul. 10, 2000.

(51) Int. Cl.$^7$ ................................................ A61B 5/00
(52) U.S. Cl. ...................................... 600/573; 606/181
(58) Field of Search ................................ 600/573, 583; 422/63; 606/182, 181

(56) References Cited

U.S. PATENT DOCUMENTS

| 4,627,445 A | * | 12/1986 | Garcia et al. ................ 600/583 |
| 4,787,398 A | * | 11/1988 | Garcia et al. ................ 600/583 |
| 4,869,249 A | * | 9/1989 | Grossman et al. ........... 606/182 |
| 5,971,941 A | * | 10/1999 | Simons et al. .............. 606/573 |
| 6,056,701 A | * | 5/2000 | Duchon et al. ............. 600/583 |
| 6,071,294 A | * | 6/2000 | Simons et al. .............. 606/181 |
| 6,159,424 A | * | 12/2000 | Kauhaniemi et al. ......... 422/63 |
| 2001/0056284 A1 | * | 12/2001 | Purcell et al. .............. 606/181 |
| 2002/0103499 A1 | * | 8/2002 | Perez et al. ................. 606/182 |

* cited by examiner

Primary Examiner—Teresa Walberg
Assistant Examiner—Leonid M Fastovsky
(74) Attorney, Agent, or Firm—Jerome L. Jeffers (57) ABSTRACT

A lance is provided for puncturing skin and producing a sample of blood. The lance comprises a spring having a first end and a second end disposed between a needle and a base wherein the first end of spring is coupled to the base and the second end of the spring is coupled to the needle.

18 Claims, 9 Drawing Sheets

THIN LANCE AND TEST SENSOR HAVING SAME

This application claims the benefit of Provisional application No. 60/216,972, filed Jul. 10, 2000.

FIELD OF THE INVENTION

The present invention relates generally to blood monitoring devices, and, more particularly, to a thin lance and a test sensor having the same for obtaining a sample of blood.

BACKGROUND OF THE INVENTION

It is often necessary to quickly obtain a sample of blood and perform an analysis of the blood sample. One example of a need for painlessly obtaining a sample of blood is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if their blood glucose level becomes too high—a condition known as hyperglycemia. Both conditions, hypoglycemia and hyperglycemia, are both potentially life-threatening emergencies.

Figure 1:
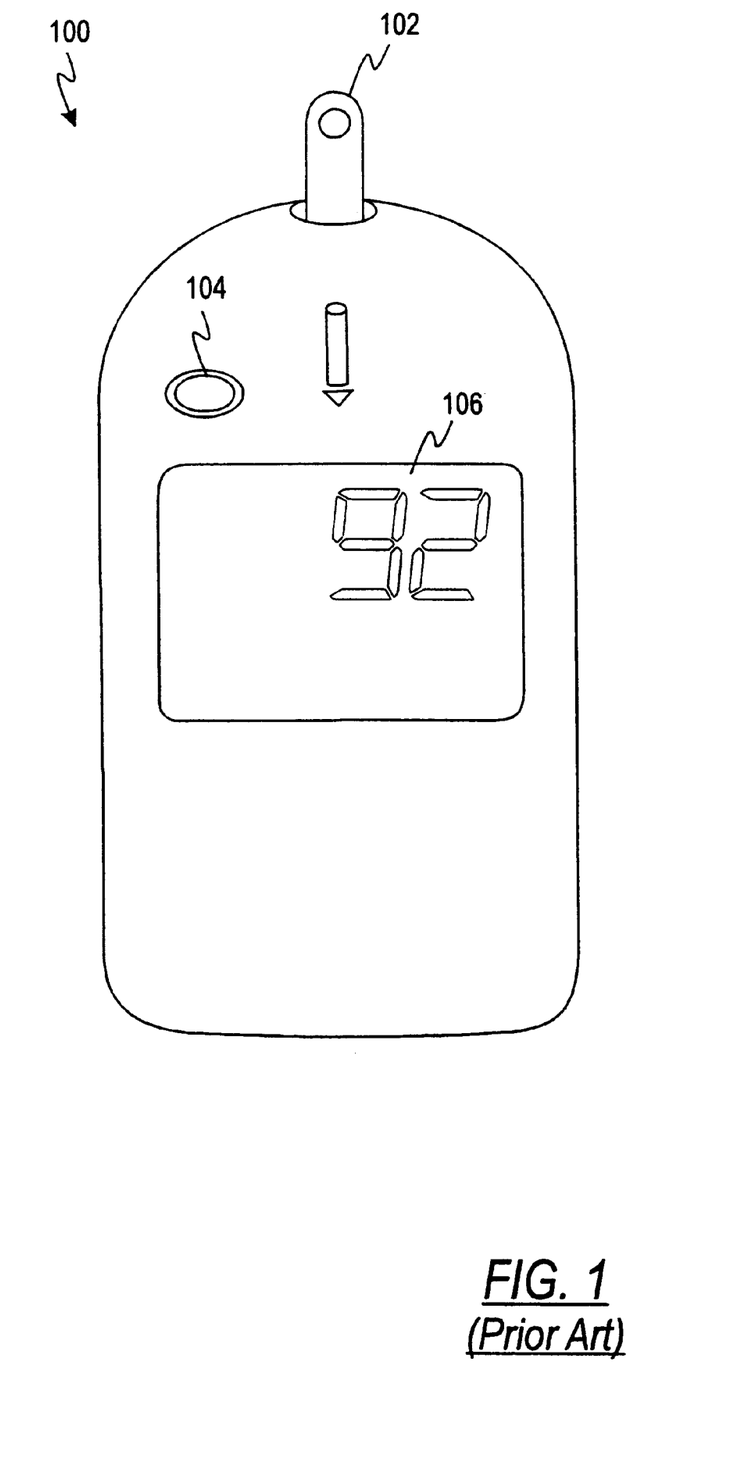
FIG. 1 is a top view of a prior art blood glucose testing device.
Figure 2:
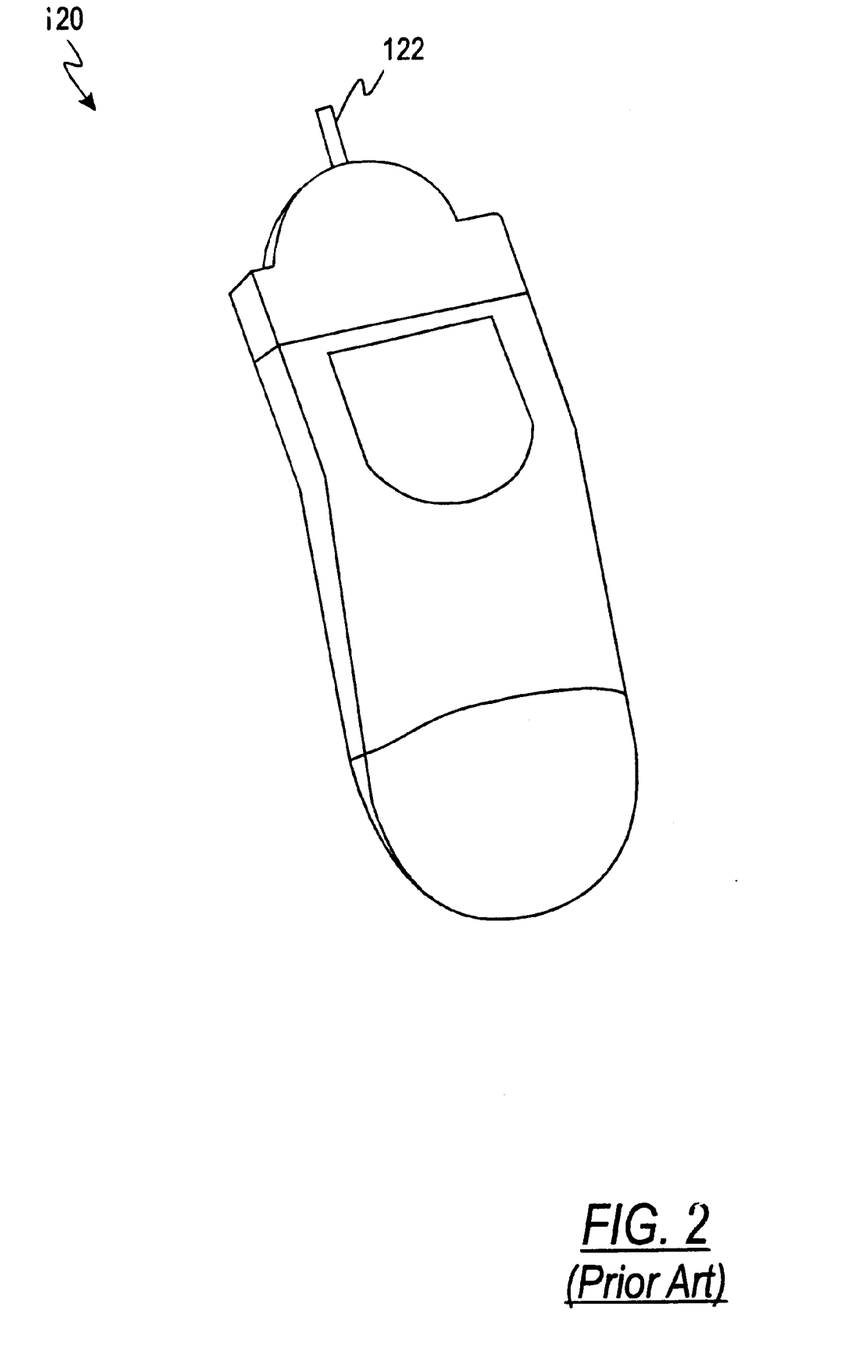
FIG. 2 is a perspective view of a prior art lance.

One method of monitoring a person's blood glucose level is with a portable, hand-held blood glucose testing device. A prior art blood glucose testing device 100 is illustrated in FIG. 1. The portable nature of these devices 100 enables the users to conveniently test their blood glucose levels wherever the user may be. The glucose testing device contains a test sensor 102 to harvest the blood for analysis. The device 100 contains a switch 104 to activate the device 100 and a display 106 to display the blood glucose analysis results. In order to check the blood glucose level, a drop of blood is obtained from the fingertip using a lancing device. A prior art lancing device 120 is illustrated in FIG. 2. The lancing device 120 contains a needle lance 122 to puncture the skin. Some lancing devices implement a vacuum to facilitate the drawing of blood. Once the requisite amount of blood is produced on the fingertip, the blood is harvested using the test sensor 102. The test sensor 102, which is inserted into a testing unit 100, is brought into contact with the blood drop. The test sensor 102 draws the blood to the inside of the test unit 100 which then determines the concentration of glucose in the blood. Once the results of the test are displayed on the display 106 of the test unit 100, the test sensor 102 is discarded. Each new test requires a new test sensor 102.

One problem associated with some conventional lancing devices is that the user who regularly self-tests is required to carry at least two instruments—a lance and a test unit. This places a greater burden on the user to remember to carry as well as to maintain two separate devices. Further, a greater amount of space is occupied on the user's person. There can also be an increased expense associated with two separate units.

Another problem associated with some conventional blood glucose monitoring devices is that the user's blood physically contacts the elements within the testing unit. Cross-contamination can be a problem if the monitoring device is used by more than one user such as in a doctor's office or other clinical setting.

SUMMARY OF THE INVENTION

A lance is provided for puncturing skin and producing a sample of blood. The lance comprises a spring having a first end and a second end disposed between a needle and a base wherein the first end of integral spring is coupled to the base and the second end of the spring is coupled to the needle.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE DRAWINGS

Other objects and advantages of the invention will become apparent upon reading the following detailed description in conjunction with the drawings in which.

DETAILED DESCRIPTION OF THE PREFERRED EMBODIMENTS

Figure 3:
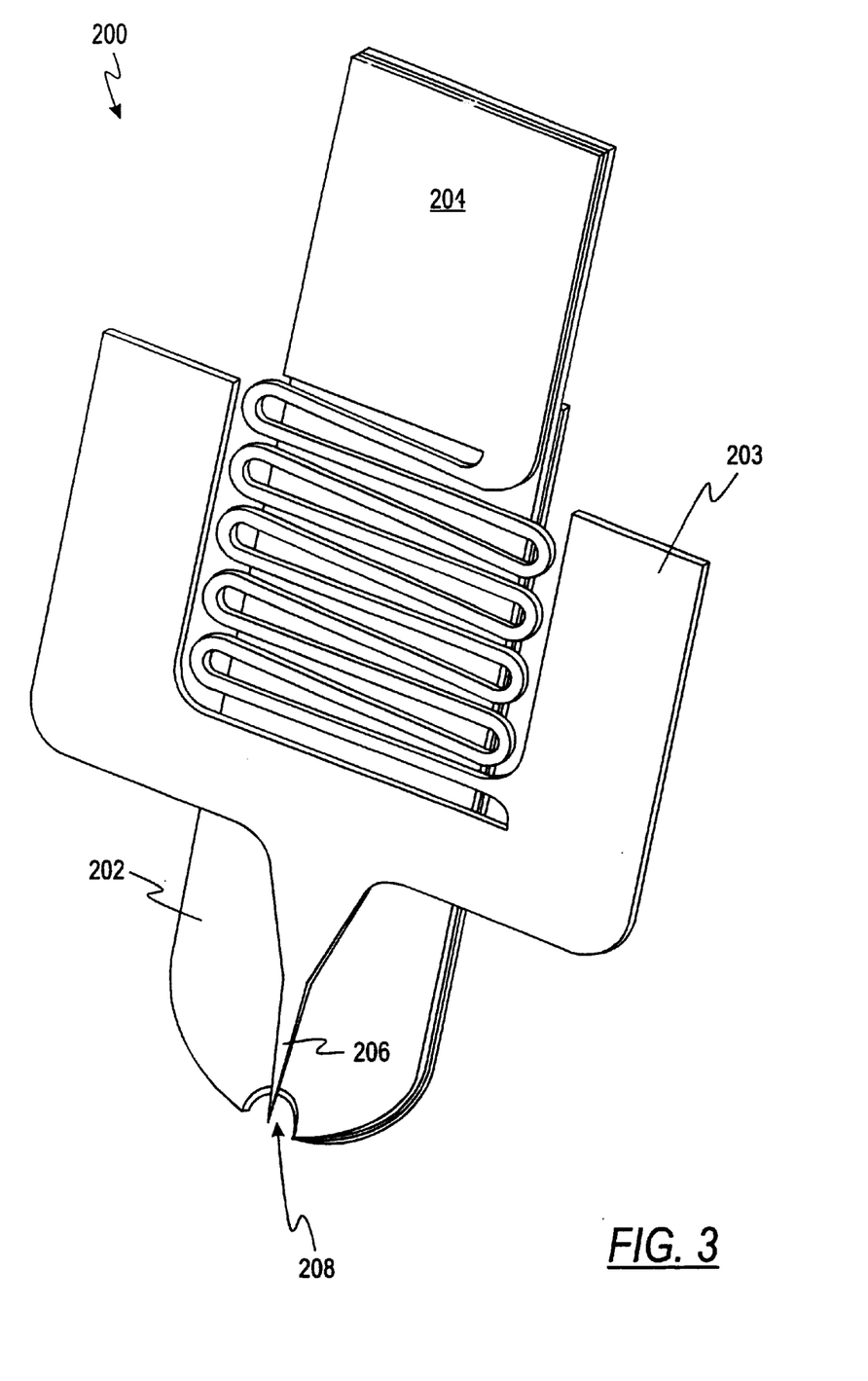
FIG. 3 is a perspective view of a test sensor having a thin lance according to one embodiment of the present invention.

Referring now to FIG. 3, a test sensor having a thin sensor and lance ("sensor/lance") 200 according to one embodiment of the present invention is illustrated. The sensor/lance 200 includes a thin test sensor 202 and a thin lance 203. The thin lance 203 has a base 204 which is coupled to the test sensor 202. The remainder of the thin lance 203 is movable allowing a thin needle 206 to travel downward to puncture a user's skin in order to produce a drop of the user's blood. The test sensor 202 has an inlet 208 through which blood is moved by capillary action into the test sensor 202. The test sensor 202 and the lance 203 are generally thin and flat and each have a thickness of approximately 0.006 inch.

Figure 4:
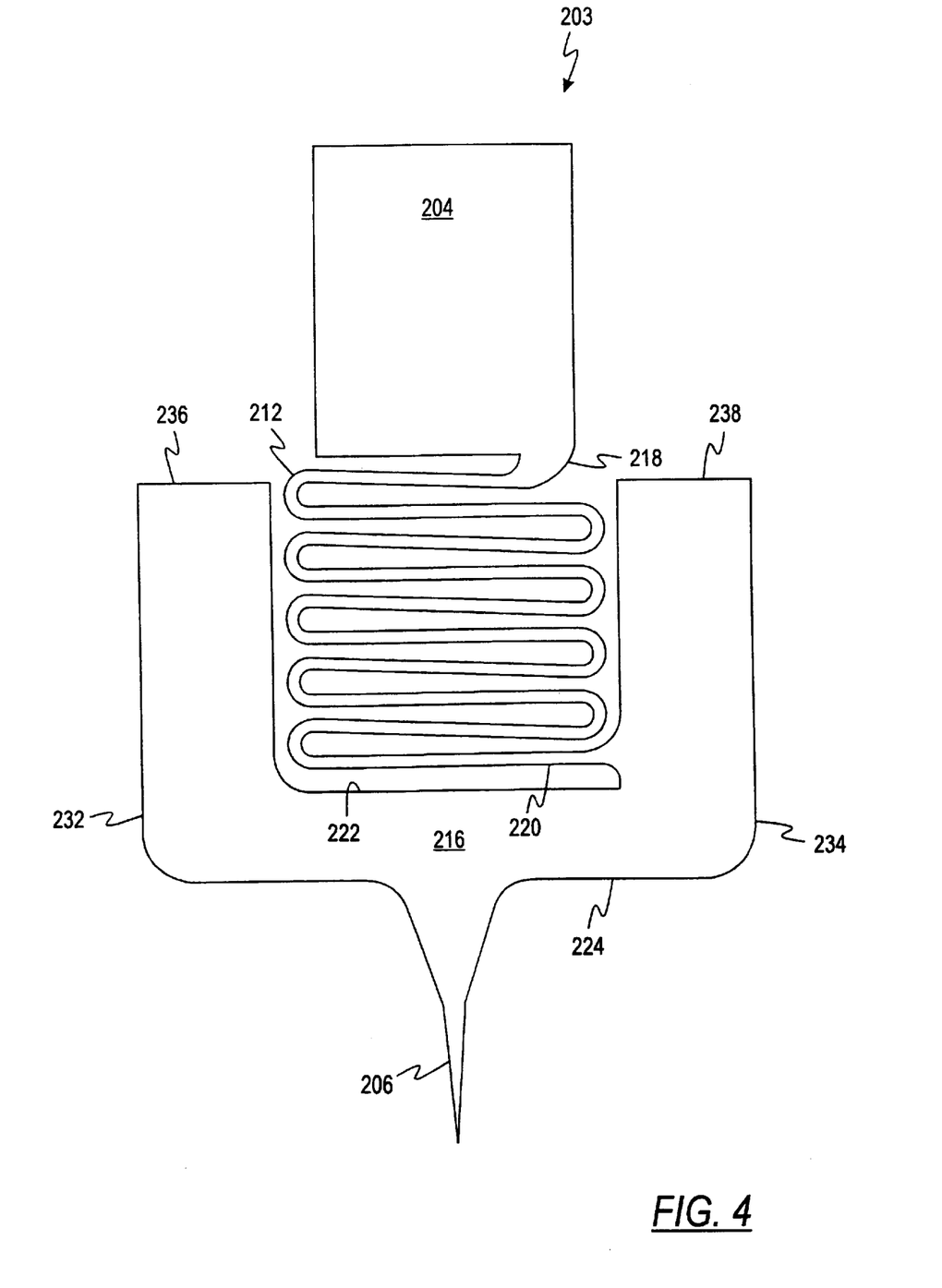
FIG. 4 is front view of a thin lance according to one embodiment of the present invention.

Referring also to FIG. 4, the thin lance 203 of the sensor/lance 200 will be described in greater detail. The illustrated embodiment of the thin lance 203 is formed out of a single piece of metal. A thin spring 212 couples the base 204 to a U-shaped member 216. The spring 212 has a first end 218 and a second end 220, the first end 218 of which is coupled to the base 204 and the second end is coupled to an interior 222 of the U-shaped member 216. The thin needle 206 is formed on an exterior 224 of the U-shaped member. The two sides of the U-shaped member are force receiving members 232,234 for providing movement to the thin needle 206.

In operation, when a user is testing the glucose concentration of blood, the test sensor 202 remains stationary within a testing device while a force is imparted on to a top portion 236,238 of each force receiving member 232,234. The force receiving members 232,234 are driven downward thus forcing the needle 206 downward into the user's skin. Once the force is removed from the force receiving members 232,234, the spring 212 retracts the needle 206 from the user's skin.

Figure 5:
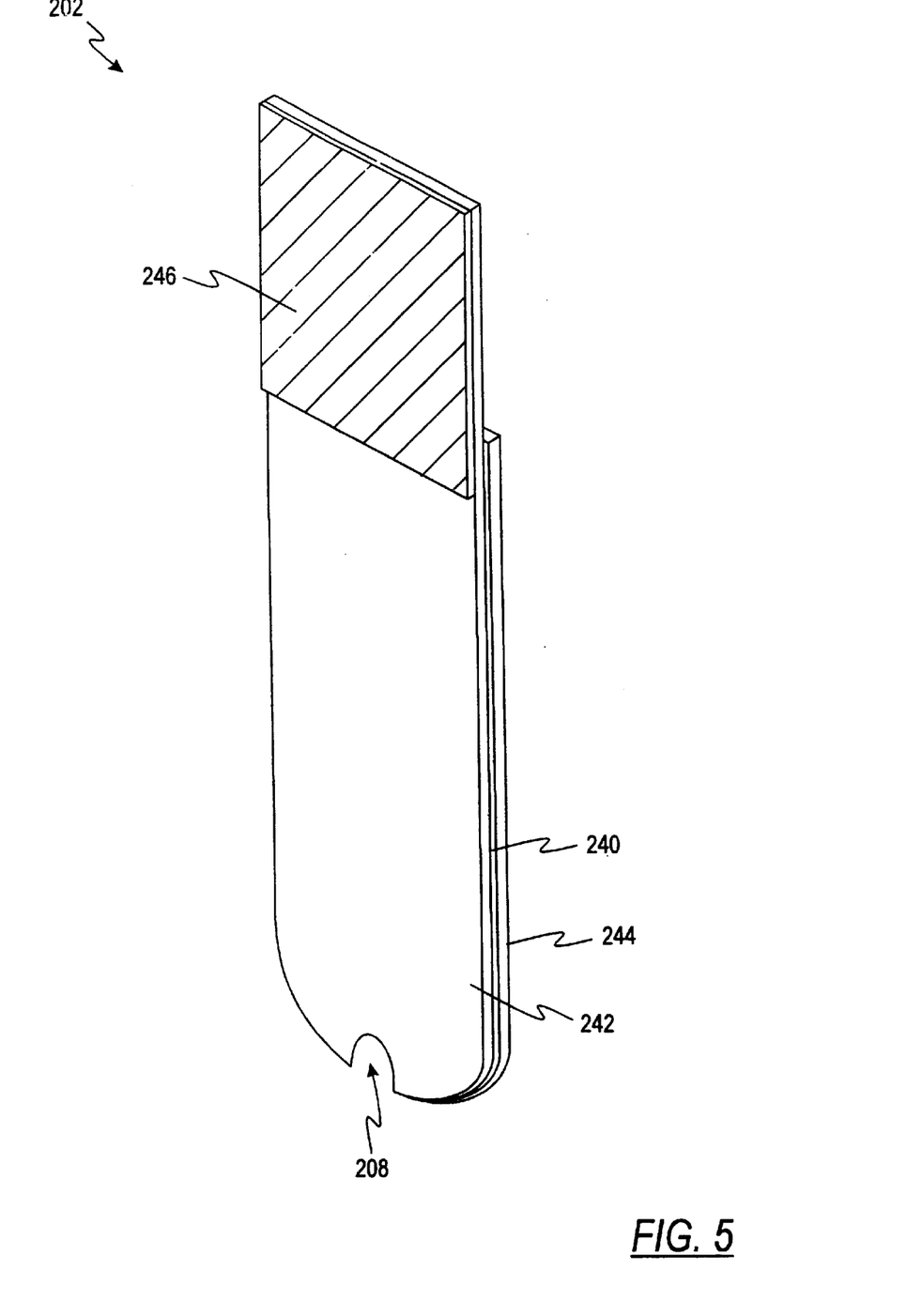
FIG. 5 is a perspective view of test sensor according to one embodiment of the present invention.
Figure 6:
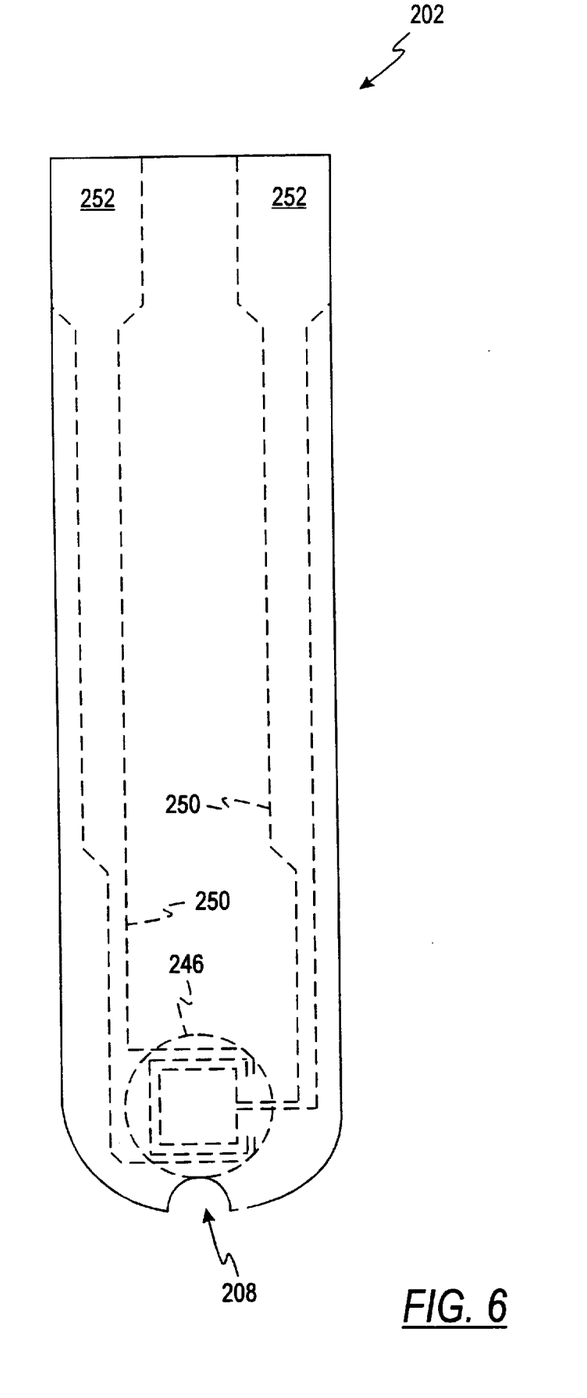
FIG. 6 is a cross-sectional view of the test sensor illustrated in FIG. 5.

Referring also to FIGS. 5 and 6, the thin test sensor 202 will be described in greater detail. The test sensor 202 comprises a test chamber having a test area 240 disposed between a front panel 242 and a rear panel 244. The test area 240 is designed to allow blood to move from the inlet 208 up the test area 240 via capillary action. An adhesive 246 is disposed on the front panel 242 to adhere the base 204 of the thin lance 203 to the front panel 240.

A reagent is incorporated into the test sensor 202. The reagent is designed to react with the glucose in the blood which moves up the test area 240. The reaction produces a detectable signal which is indicative of the glucose concentration in the sample of blood. That signal is then measured by a sensor which can measure the concentration of the glucose in the blood based on the signal. The specific reagent incorporated into the test sensor 202 is a function of the type of sensing employed to determine the concentration of glucose in the blood. In the illustrated embodiment of the test sensor 202, electrochemical sensing is employed. The test sensor 202 includes a pair of electrodes 250 (FIG. 6). It electrochemical analysis, the change in current across the electrodes 250 caused by the reaction of the glucose and the reagent is indicative of the concentration of the glucose in the blood. The reaction of the glucose and the reagent creates an oxidation current at the electrodes 250 which is directly proportional to the user's blood glucose concentration. This current can be measured by an appropriate sensor coupled to a pair of terminals 252 corresponding to the electrodes 250 implemented in a glucose monitoring device for use with the sensor/lance 200. The glucose monitoring device can then communicate to the user the blood glucose concentration. An example of an electrochemical testing system is described in detail by commonly-owned U.S. Pat. No. 5,723,284 entitled "Control Solution and Method for Testing the Performance of an Electrochemical Device for Determining the Concentration of an Analyte in Blood" which is incorporated herein by reference in its entirety.

Figure 7:
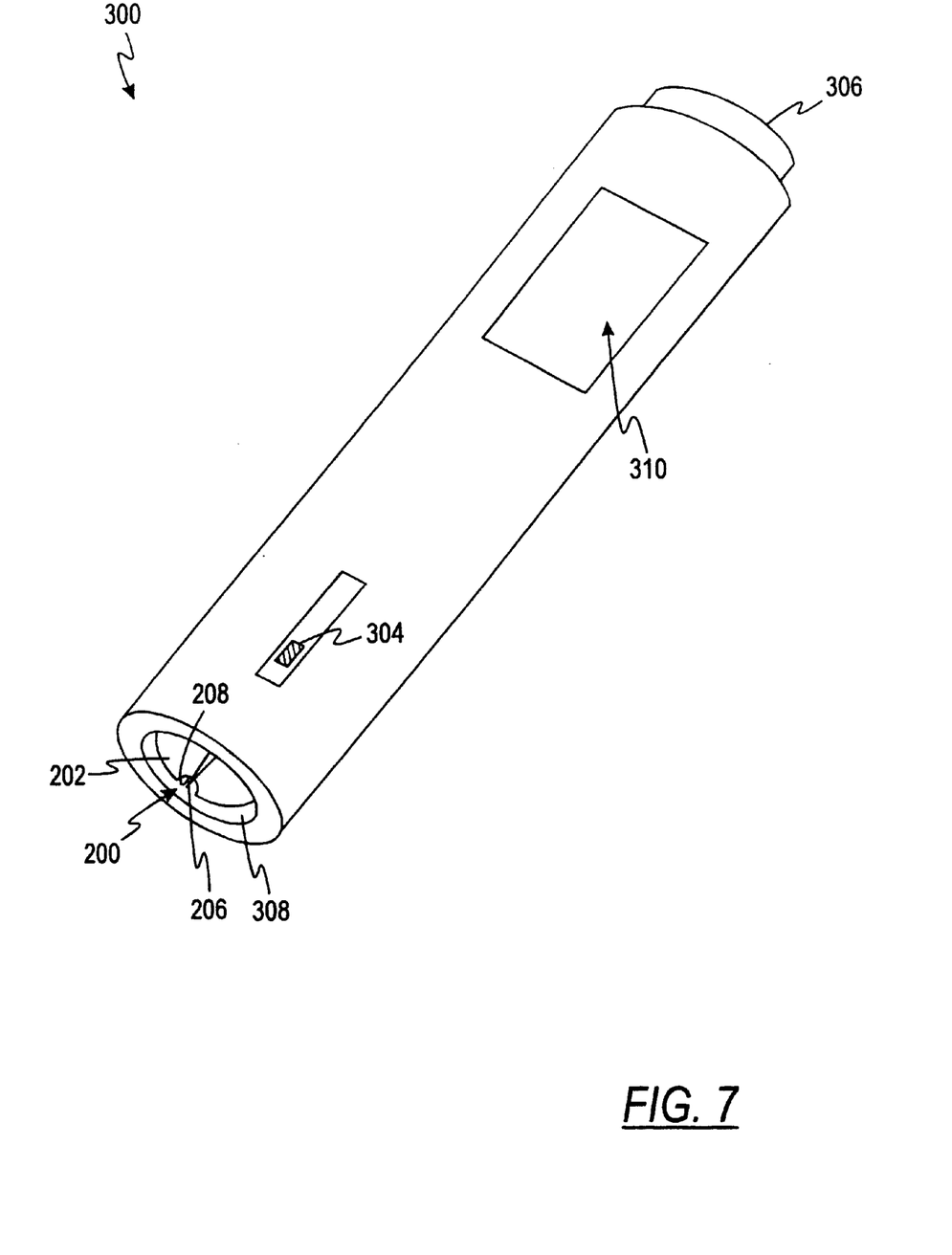
FIG. 7 is an embodiment of a blood glucose monitoring system for use in conjunction with a test sensor having a thin lance according to an alternative embodiment of the present invention.

Referring now to FIG. 7, an application of the sensor/lance 200 is in an integrated blood glucose monitoring system 300 which integrates the lancing, the blood harvesting, and a blood glucose analyzer into a single instrument. The integrated blood glucose monitoring system 300 contains a plurality of sensors/lances 200 for use in a plurality of blood glucose self-tests. In operation, a user would activate the system 300 with a switch 304. A new thin sensor/lance 200 is advanced to the test end 302 of the system 300. The user would then press the test end 302 of the system against the user's skin and depress a trigger 306 causing a spring loaded member (not shown) to apply a force to the force receiving members 232,234 of the thin lance 203. The needle 206 would then extend through an opening 308 in the test end 302 of the system 300 to puncture the user's skin. After the needle 206 is fully extended out of the opening 308, the spring 214 would withdraw the needle from the laceration created in the user's skin through the opening 308. Blood emerging from the laceration created in the user's skin is moved from the inlet 208 by capillary action into the test sensor 202. Once the requisite blood sample has been obtained and the requisite time has elapsed for the reaction in the test sensor 202 to take place, the blood glucose monitoring system 300 measurers the signal produced by the reaction and determines the blood glucose concentration of the blood sample. The results of the analysis are communicated to the user via a display 310. The sensor/lance 200 is then ejected from the system 300 and discarded.

Figure 8:
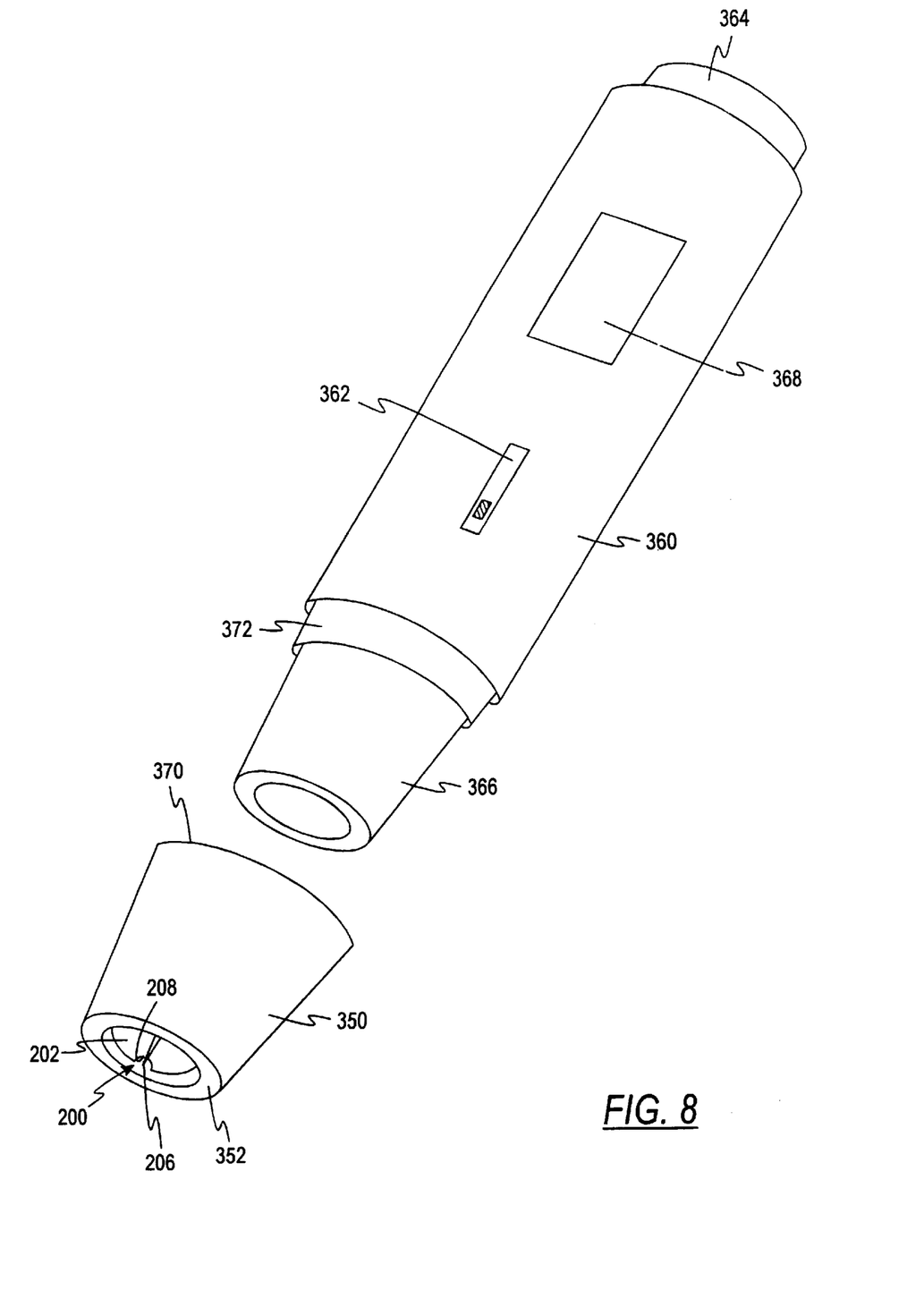
FIG. 8 is a prospective view of an end cap and a blood glucose monitoring system for use in conjunction with a test sensor having a thin lance according to a second alternative embodiment of the present invention.
Figure 9A:
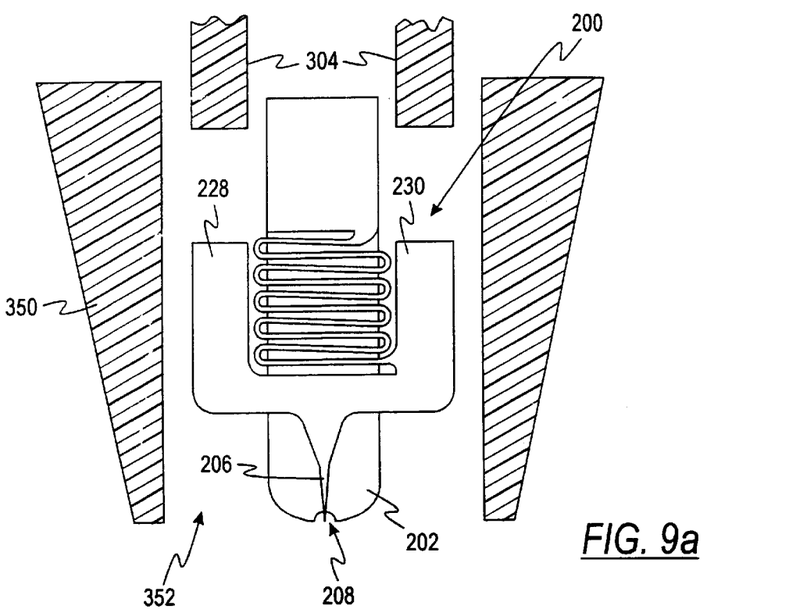
FIG. 9*a* is a cross-sectional view of the end cap illustrated in FIG. 8.
Figure 9B:
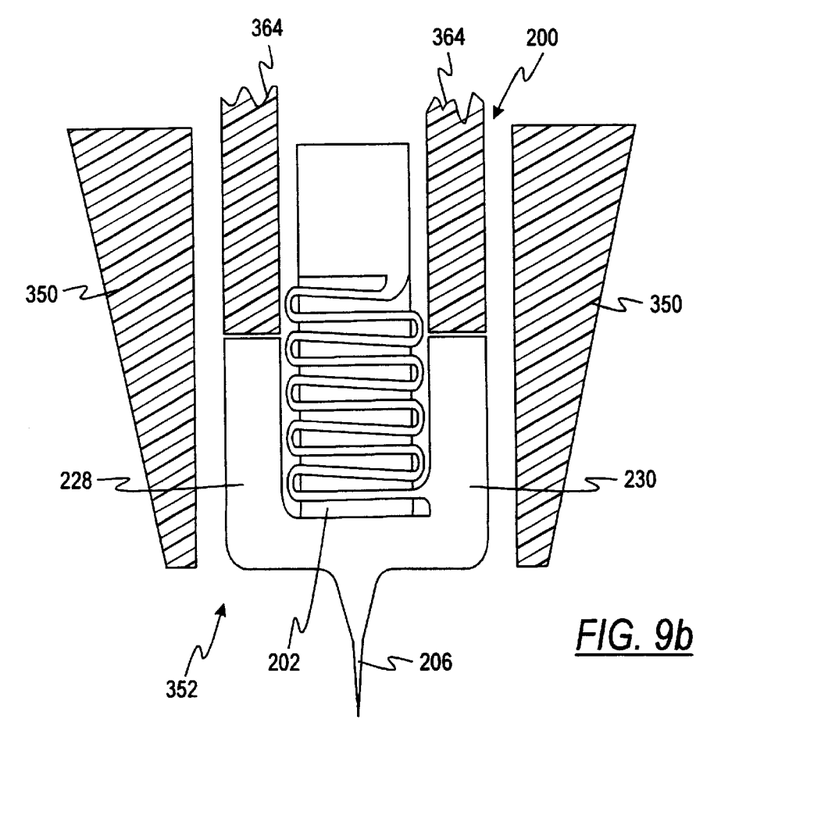
FIG. 9*b* is a cross-sectional view of the end cap illustrated in FIG. 8 with the thin lance extended.

Referring now to FIGS. 8, 9a, and 9b, another application of the sensor/lance 200 is in a disposable, protective end cap 350. In a clinical setting, such as a medical doctor's office where the user is a doctor, nurse, or technician seeing multiple patients, cross contamination is a serious concern. Obviously, components of medical devices which come into contact with one patient's blood can not come into contact with the user or another patient. The end cap 350 protects those who handle the end cap 350 from coming into contact with the needle 206 and any blood disposed thereon after the sensor/lance 200 within the end cap 350 have been used. Only when actuated (during testing), does the needle 206 extend beyond the area bounded by the end cap 350. Accordingly, a user (doctor, nurse, technician) is protected from being punctured with the needle 206 when connecting the end cap 350 to or removing the end cap 350 from the sensor/lance 200.

A blood glucose monitoring system 360 for use with the disposable end cap 350 having a sensor/lance 200 disposed therein is also illustrated in FIG. 8. The device 360 contains a switch 362 to activate the device 360. A trigger 364 is provided to fire a spring loaded plunger 366 to contact the force receiving members 232,234 which in turn provide movement to the needle 206. The when actuated, the spring loaded plunger 366 rapidly moves downward a predetermined distance to move the force receiving members 232, 234 and in turn the needle 206 a predetermined distance causing the needle 206 to extend beyond a test end 352 of the end cap 350 a distance about equal to the needle 206 penetration depth. The distance that the needle 206 extends beyond the test end 352 of the end cap 350 is preferably a distance sufficient to draw a sample of blood for analysis. Once the plunger forces the needle downward, the spring loaded plunger 366 retracts a distance allowing the needle 206 to retract back within the bounds of the disposable end cap 350. Meanwhile, the sample of blood moves though the inlet 208 disposed adjacent to the test end 352 of the end cap 350) of the test sensor 202. Once the requisite blood sample has been obtained and the requisite time has elapsed for the reaction in the test sensor 202, the blood glucose monitoring system 360 measurers the signal produced by the reaction and determines the blood glucose concentration of the blood sample. The results of the analysis are communicated to the user via a display 368. The end cap 350 containing the used sensor/lance 200 is then removed from the system 300 and discarded. The end cap 350 and the blood glucose monitoring system 360 have suitable connectors 370, 372 for mating the end cap 350 with the blood glucose monitoring system 360.

Thus far, only electrochemical analysis to determine the glucose concentration of a blood sample has been discussed in conjunction with the present invention. However, the thin sensor/lance 203 of the present invention can be used with other types of blood glucose testing methods. For example, calorimetric testing may be implemented in the test sensor in conjunction with an alternative embodiment of the present invention. Colorimetric testing is described in commonly-owned U.S. Pat. No. 5,723,284 entitled "Control Solution and Method for Testing the Performance of an Electrochemical Device for Determining the Concentration of an Analyte in Blood," which was incorporated herein by reference above.

While the invention is susceptible to various modifications and alternative forms, specific embodiments thereof have been shown by way of example in the drawings and will be described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. A test sensor for use in the determination of the concentration of a chemical in blood, the test sensor comprising:
   a front and a rear panel;
   a substantially flat test chamber disposed between the front and rear panels having an inlet, the test chamber being adapted to collect a sample of blood through the inlet; and
   a substantially flat lance coupled to one of the front and rear panels, the lance being adapted to puncture skin.

2. The test sensor of claim 1 wherein the lance includes:
   a spring having a first end and a second end, the first end coupled to the test sensor; and
   a needle coupled to the second end of the spring.

3. The test sensor of claim 1 wherein the lance includes:
   a base;
   a thin spring having a first end and a second end, the first end coupled to the base;
   a thin, generally U-shaped body having an interior edge and an exterior edge, the second end of the thin spring coupled to the interior edge; and
   a thin needle coupled to the exterior edge.

4. The test sensor of claim 1 wherein the test chamber includes a reagent, the reagent being adapted to produce an electrochemical reaction, the test sensor further comprising a pair of electrodes coupled to the test chamber.

5. The test sensor of claim 3 in combination with a sensor adapted to measure the concentration of a chemical in the blood.

6. The test sensor of claim 1 wherein the lance has a thickness of about 0.006 inch.

7. A lance comprising:
   a substantially flat base;
   a substantially flat spring having a first end and a second end, the first end of the spring being attached to the base;
   a substantially flat, generally U-shaped body having an interior edge and an exterior edge, the interior edge of the U-shaped body coupled to the second end of the spring, the generally U-shaped body having two sides for receiving an external force providing movement to the U-shaped member; and
   a substantially flat needle attached to the exterior edge of the U-shaped body;
   wherein, the base, the spring, the U-shaped body, and the needle are made out of a single piece of a material.

8. The lance of claim 7 wherein the single piece of material is a metal.

9. The lance of claim 7 wherein the base, the spring, the U-shaped body, and the needle are approximately 0.006 inch thick.

10. The lance of claim 7 further comprising a substantially flat test sensor for use in the determination of the concentration of a chemical in blood, the base of the lance being attached to the substantially flat test sensor such that an inlet of the test sensor is disposed proximate the substantially flat needle.

11. A blood glucose monitoring system comprising:
    a substantially flat test sensor having an inlet for receiving a blood sample;
    a substantially flat lance having a substantially flat base, a substantially flat spring, and a substantially flat, generally U-shaped body, the spring having first and second end, the first end being attached the base, the U-shaped body having an interior edge attached to the second end of the spring and an exterior edge, the lace having a substantially flat needle outwardly extending from the exterior edge of the U-shaped body for puncturing a user's skin; and
    a forcing member providing movement to the needle of the lance in a first direction by contacting the U-shaped body, the spring retracting the flat lance in a second direction.

12. The system of claim 11 wherein the substantially flat, generally U-shaped body comprises two side portions for receiving a force from the force providing member.

13. The system of claim 11 wherein the substantially flat lance and the substantially flat test sensor are disposed in a disposable cap.

14. The system of claim 11 wherein the test sensor includes a reagent adapted to produce an electrochemical reaction indicative the concentration of glucose in the receive blood sample, the test sensor further comprising a pair of electrodes.

15. The system of claim 11 in combination with a device for measuring the concentration of the glucose in the blood.

16. The system of claim 11 wherein the substantially flat base, the substantially flat spring, the substantially flat, generally U-shaped body, and the a substantially flat needle are formed from a single piece of material.

17. The system of claim 16 wherein the material is metal.

18. The system of claim 11 wherein the substantially flat base, the substantially flat spring, the substantially flat, generally U-shaped body, and the a substantially flat needle are approximately 0.006 inch thick.

* * * * *